(12) United States Patent
Ehrnsperger et al.

(10) Patent No.: US 6,764,476 B1
(45) Date of Patent: Jul. 20, 2004

(54) ABSORBENT ARTICLE COMPRISING A LIQUID HANDLING MEMBER THAT RAPIDLY DISTRIBUTES ACQUIRED LIQUID

(75) Inventors: Bruno Johannes Ehrnsperger, Frankfurt (DE); Stephen Allen Goldman, Wyoming, OH (US); Mattias Schmidt, Idstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/720,192

(22) PCT Filed: Jun. 29, 1999

(86) PCT No.: PCT/US99/14795

§ 371 (c)(1),
(2), (4) Date: Dec. 20, 2000

(87) PCT Pub. No.: WO00/00149

PCT Pub. Date: Jan. 6, 2000

(30) Foreign Application Priority Data

| Jun. 29, 1998 | (WO) | PCT/US98/13449 |
|---|---|---|
| Jun. 29, 1998 | (WO) | PCT/US98/13497 |
| Jun. 29, 1998 | (WO) | PCT/US98/13521 |
| Jun. 29, 1998 | (WO) | PCT/US98/13523 |

(51) Int. Cl.$^7$ ................................................ A61F 13/15
(52) U.S. Cl. .............................. 604/385.101; 604/378; 604/367
(58) Field of Search .......................... 604/358, 385.101, 604/367, 369, 368, 372–377, 378, 379, 380, 370

(56) References Cited

U.S. PATENT DOCUMENTS

| 5,562,646 A | 10/1996 | Goldman et al. |
| 5,599,335 A | 2/1997 | Goldman et al. |

FOREIGN PATENT DOCUMENTS

| WO | WO 94/13704 | 6/1994 |
| WO | WO 98/07909 | 2/1998 |
| WO | WO 98/22065 | 5/1998 |
| WO | WO 00/00129 | 1/2000 |
| WO | WO 00/00136 | 1/2000 |
| WO | WO 00/00138 | 1/2000 |
| WO | WO 00/00143 | 1/2000 |
| WO | WO 00/00146 | 1/2000 |

*Primary Examiner*—Weilun Lo
*Assistant Examiner*—Jacqueline F Stephens
(74) *Attorney, Agent, or Firm*—Edward J. Milbrada; Eileen L. Hughett; Ken K. Patel

(57) ABSTRACT

The present invention provides liquid handling member which is capable of rapidly distributing the acquired liquid parallel to its surface. The present invention further provides a device for handling urine which comprises the liquid handling member.

13 Claims, No Drawings

ABSORBENT ARTICLE COMPRISING A LIQUID HANDLING MEMBER THAT RAPIDLY DISTRIBUTES ACQUIRED LIQUID

FIELD OF THE INVENTION

The present invention relates to liquid handling members intended to be used in devices for handling urine. In particular, the present invention relates to those liquid handling members which are used for initial acquisition of the urine. The present invention further relates to devices for handling urine such as diapers, training pants, adult incontinence devices, bed mats, and the like which comprises the liquid handling members of the present invention.

BACKGROUND

Devices for handling urine such as diapers, training pants, adult incontinence devices, bed mats, and the like are well known in the art and are frequently used for example for babies, toddlers, incontinent persons, and bed-ridden persons. Typically, these devices comprise liquid handling members which are specifically designed for the rapid initial acquisition of urine disposed onto the device.

It has been recognized in the prior art that it is beneficial for example for the wearing comfort of such a device for handling urine to transport the acquired urine away from the point of acquisition already in the liquid handling member. Providing sufficient void space in the liquid handling member below the point of acquisition requires the liquid acquisition member to have a high caliper and hence to be very bulky. This problem can only be avoided if the acquired urine is transported away from the point of acquisition in a direction parallel to the surface of the liquid handling member.

The most commonly used mechanism for liquid transportation is capillary pressure. It is to be noted in this context that liquid transportation requires high capillary suction which in turn requires small capillaries to build up that suction. But in the case of liquid handling members which are intended for liquid acquisition large capillaries are needed to provide the void space for quickly acquiring the urine. Thus, in the case of the above described liquid handling members wicking liquid away from the point of liquid acquisition by means of capillary pressure is not very efficient.

As a result, it may be observed in prior art devices for handling urine that only a small fraction of the x, y-dimension of the liquid handling member is actually used when the first gush of urine is acquired. Hence, the void volume and liquid acquisition performance of the liquid handling member is not fully utilized.

It is therefore an object of the present invention to provide a liquid transport member which overcomes the problems posed by the prior art.

It is a further object of the present invention to provide a liquid handling member which distributes already the first gush of urine over a large fraction of its x, y-dimension.

It is a further object of the present invention to provide the liquid handling member which can acquire liquid while maintaining a relatively small wet caliper.

It is a further object of the present invention to provide a device for managing body liquids which comprises a liquid transport member of the present invention.

SUMMARY OF THE INVENTION

The present invention provides a liquid handling member for use and device for handling urine. The liquid handling member has an x, y-dimension of at least 60 square centimeters and the liquid handling member has a first gush distribution area of at least 80 percent of said x, y-dimension according to the member liquid distribution test defined herein.

The present invention provides a liquid handling member for use and device for handling urine. The liquid handling member has an x-dimension of at least 15 centimeters and the liquid handling member has a first gush distribution length of at least 80 percent of said x-dimension according to the member liquid distribution test defined herein.

The present invention further provides a device for handling urine comprising a first member for temporary storage of the acquired urine. The first member has an x, y-dimension of at least 60 square centimeters. The first member further has a first gush distribution area of at least 80 percent of said x, y-dimension of said acquisition member according to the member liquid distribution test defined herein.

The present invention further provides a device for handling urine comprising a first member for temporary storage of the acquired urine. The first member has an x-dimension of at least 15 centimeters. The first member further has a first gush distribution length of at least 80 percent of said x-dimension of said acquisition member according to the member liquid distribution test defined herein.

DETAILED DESCRIPTION OF THE INVENTION

The present invention is described in the following by means of a variety of different embodiments and by means of a variety of different features. Further embodiments of the present invention may be obtained by combining features of one embodiment with features of another embodiment disclosed herein and/or with other features disclosed herein. These further embodiments are considered to be implicitly disclosed herein and hence form part of the present invention. It will be apparent to the skilled person that combinations of certain features may lead to non-functional articles not forming part of this present invention.

The following description is adopted for devices for handling body liquids of the baby diaper type, and in particular for devices intended for babies in the weight range of about 9–18 kg. Nonetheless, the skilled person will be able to readily adopt it for other purposes, such as for other sizes, or adult incontinence applications. The average gush size for the above babies is 75 ml, the 95 percentile of their gush size is 110 ml. The average urination rate for the above babies is 15 ml per second, the 95 percentile of their size is 22 milliliters per second. In adult incontinence context, the average gush size is 110 milliliters and average urination rate is at 22 ml per second. Nonetheless, gushes in the adult incontinence context may be up to 180 milliliters with peak rates up to 40 ml/s.

The present invention provides a liquid handling member which is intended to be used for the initial rapid acquisition of liquid gushes disposed onto a device for handling urine. The present invention further provides a device for handling urine comprising such a liquid handling member. The device of the present invention may be used for example as diapers, training pants, adult incontinence devices, or the like.

The term "liquid handling device" as used herein refers to devices which are designed to handle body liquids such as urine, menses, feces, and the like. Handling body fluids includes but is not limited to acquiring, distributing, and storing the body liquids.

The device for handling urine according to the present invention further comprises a liquid acquisition region.

The term "acquisition region" as used herein refers to that region of the device for handling urine according to the present invention which is intended to first come into contact with the exudated body liquids. In many cases, the acquisition region of the device is distinguished from other regions of the device by for example different materials. In this case, the acquisition region comprises the total surface area covered by the specific acquisition material. In cases where the acquisition region is not distinguished from other regions in their readily apparent way, the acquisition region is considered to be that region which is centered around the intended loading point of the device, which is about a third of the length of the device long, and which spans over the entire width of the device. In case, more than one loading point is foreseen in the intended use of the device, the geometric average of these loading points is to be used for the definition of the acquisition region.

For the purpose of the present invention, a Cartesian coordinate system is defined as follows. The. z-direction is defined to be perpendicular to the surface of the acquisition region at the intended loading point. The x-direction is defined to coincide with the longitudinal dimension of the device for handling urine. In the case of a diaper, the x-direction runs from the front region of the device (which comes into contact with the front waist region of the wearer during use) to the back region of the device (which comes into contact with a back waist region of the wearer during use). Accordingly, the y-direction coincides with a transverse dimension of the device for handling urine which runs from the left to the right of the wearer during use. It is to be understood in this context that this Cartesian coordinate system is only a truly Cartesian coordinate system when the device is in the flat out configuration. For typical in use conditions, the configuration of the device is such that x-, y-, and z-direction as defined above only form a locally perpendicular set of coordinates.

A liquid handling member of the present invention rapidly distributes acquired liquid over large fraction of its x, y-dimension. This rapid distribution of liquid is independent of gravitational forces acting on the liquid. This enables the liquid handling member of the present invention to achieve this rapid distribution also in those in use configurations in which the liquid has to be distributed against gravity. For the purposes of this invention, the ability of a liquid handling member to rapidly distribute liquid over its x, y-dimension or along its x-dimension is quantified by the member liquid distribution test defined hereinafter. A liquid handling member of the present invention has a liquid distribution ratio of at least 80 percent, preferably a liquid distribution ratio of at least 90 percent, more preferably liquid distribution ratio of at least 95 percent, is most preferably liquid distribution ratio of at least 100 percent.

The liquid handling member of the present invention has a x, y-dimension of at least 60 square centimeters, preferably of at least 90 square centimeters, more preferably of at least 130 square centimeters, most preferably of at least 180 square centimeters. The surface area dimensions are intended to be used for devices having a target user group of babies in the weight range between 9 and 18 kg. For other target user groups which may have different urination patterns as can be seen for example in different gush sizes, the aforementioned surface area dimensions have to be adopted accordingly. Alternatively, the liquid handling member of the present invention has a x-dimension of at least 15 centimeters, preferably of at least 18 centimeters, more preferably of at least 20 centimeters, most preferably of at least 25 centimeters. Again, this x-dimension is given for intended user group of babies in the weight range between 9 and 18 kilograms. For other intended user groups, this dimension also needs to be adopted accordingly.

It is further desirable for the liquid handling member of the present invention to exhibit a high absorbent capacity in order to be able to a readily acquire larger loads of liquid. For the purpose of this invention, the absorbent capacity of the liquid handling member is quantified by the demand absorbency test defined hereinafter, Preferably, the liquid handling member of the present invention has an absorbent capacity of at least 50 ml, more preferably of at least 75 ml, yet more preferably of at least 110 ml, most preferably of at least 180 ml.

It is further desirable for the liquid handling member of the present invention to exhibit a high trans-planar and in-plane permeability in order to be able to rapidly distribute acquired liquid over its x-and, y-directions. For the purposes of this invention, the permeability is measured via the permeability test defined in PCT patent application No. US98/13497 filed on Jun. 29, 1998 incorporated herein by reference. Preferably, the liquid handling member of the present invention has a permeability of at least 10 Darcy, more preferably a permeability of at least 50 Darcy, most preferably a permeability of at least 100 Darcy.

It is desirable for the liquid handling member of the present invention to only have a small caliper, i.e. a small z-direction dimension. A smaller caliper of the liquid handling member leads to less bulk between the legs of the wearer. Preferably, the liquid handling member according to the present invention has a z-direction dimension of less than 30 mm, more preferably of less than 20 mm, most preferably of less than 15 mm.

It is desirable for the liquid handling member according to the present invention to have a y-direction dimension in the vicinity of the intended loading point which is as small as possible in order to not exhibit high bulk between the legs of the wearer. Preferably, the liquid handling member according to the present invention has a y-direction dimension in the vicinity of the intended loading point of less than 100 milliliters, more preferably of less than 80 milliliters, most preferably of less than 60 mm.

The present invention further provides a device for handling urine comprising a first member for temporary storage of the acquired during and a second member for the ultimate storage of the acquired urine. In this context, the liquid handling member of the present invention may be used for example as the first member of the device for handling urine.

Liquid Transport Member

In the following, a suitable embodiment of the liquid handling member will be described. The liquid handling member is assembled from an open celled foam material which is completely enveloped by a membrane. A suitable membrane material is available from SEFAR of Rüschlikon, Switzerland, under the designation SEFAR 03-20/14. A suitable foam material is available from Recticel of Brussels, Belgium, under the designation Bulpren S10 black. A suitable technique to completely envelope the foam material with the membrane material is to wrap the membrane material around the foam material and to subsequently heat seal all open edges of the membrane material. It will be readily apparent to the skilled practitioner to choose other similarly suitable materials. Depending on the specific intended application of the liquid handling member, it may also be required to choose similar materials with slightly different properties. After assembly, the liquid handling member is activated by immersing the liquid handling member in water or in synthetic urine until the liquid handling member is completely filled with liquid and until the membranes are completely wetted with liquid. After activation, a part of the liquid inside the liquid handling member may be squeezed out by applying an external pressure to the liquid handling member. If the activation of the liquid handling member was successful, the liquid handling member should not suck air through the membranes.

Other liquid handling members suitable for the purposes of the present invention are described for example in the PCT patent application No. PCT/US98/13497 entitled "Liquid transport member for high flux rates between two port regions" filed in the name of Ehrnsperger et al. filed on Jun. 29, 1998, and in the following PCT patent applications co-filed with the present application entitled "High flux liquid transport members comprising two different permeability regions" (P&G case CM1840MQ Ser. No. 09/720, 186, pending) filed in the name of Ehrnnsperger et al., "Liquid transport member for high flux rates between two port regions" (P&G case CM1841MQ Ser. No. 09/720,187, pending) filed in the name of Ehrnspergeret al., "Liquid transport member for high flux rates against gravity" (P&G case CM1842MQ) Ser. No. 09/720,188, now abandoned filed in the name of Ehrnsperger et al., "Liquid transport member having high permeability bulk regions and high bubble point pressure port regions" (P&G case CM1843MQ) Ser. No. 09/720,189, now abandoned filed in the name of Ehrnsperger et al. All of these documents are enclosed herein by reference.

The particular geometry of the liquid handling member of the present invention can be varied according to the specific requirements of the intended application. If, for example, the liquid handling member is intended to be used in an absorbent article the liquid handling member may be defined such that its zone of intended liquid acquisition fits between the legs of the wearer and further that its intended liquid discharge zone matches the form of the storage member associated to it. Accordingly, the outer dimensions of the liquid handling member such as length, width, or thickness may also be adapted to the specific needs of the intended application. In this context, it has to be understood, however, that the design of the outer form of the liquid handling member may have an impact on its performance. For example, the cross section of the liquid handling member directly impacts on its flow rate.

For application of the liquid handling member in a device for handling urine according to the present invention, the liquid handling member may be combined with a storage member. The term "liquid storage member" refers to a device which is capable of acquiring and storing liquid. The volume of the liquid storage member may vary with the amount of stored liquid such as by swelling. Typically, the storage member will imbibe the liquid by means of capillary suction and/or osmotic pressure. Other storage members may also use vacuum as a means to store the liquid. The liquid storage member is further capable of holding at least a portion of the stored liquid under pressure. Suitable storage members are well known in the art and may comprise for example a super absorbent polymeric material such as polyacrylate. The storage member may further comprise a fibrous structure, such as a pad of cellulosic fibers, in which the particulate superabsorbent material is dispersed. A suitable superabsorbent material is ASAP400 available from Chemdal Ltd., United Kingdom. In order to pick up the liquid discharged from the liquid handling member, the storage member may be placed in direct liquid communication with the intended liquid discharge zone of the liquid handling member.

Further examples of suitable superabsorbent polymers, often also referred to as "hydrogel forming polymer" or "absorbent gelling material", are described in U.S. Pat. No. 5,562,646 (Goldman et al.), issued Oct. 8, 1996 and U.S. Pat. No. 5,599,335 (Goldman et al.), issued Feb. 4, 1997.

In one embodiment of the present invention, the liquid handling member of the present invention is geometrically saturated or substantially geometrically saturated with free liquid. The term "free liquid" as used herein refers to liquid which is not bound to a specific surface or other entity. Free liquid can be distinguished from bound liquid by measuring the proton spin relaxation time $T_2$ of the liquid molecules according to NMR (nuclear magnetic resonance) spectroscopy methods well known in the art.

The term "geometrically saturated" as used herein refers to a region of a porous material in which the liquid accessible void spaces have been filled with a liquid. The void spaces referred to in this definition are those which are present in the current geometric configuration of the porous material. In other words, a geometrically saturated device may still be able to accept additional liquid by and only by changing is geometric configuration for example by swelling, although all voids of the device are filled with liquid in the current geometric configuration. A device for handling liquids is called geometrically saturated, if all porous materials that are part of the device and intended for liquid handling are geometrically saturated.

The term "porous material" as used herein refers to materials that comprise at least two phases—a solid material and a gas or void phase—and optionally a third liquid phase that may be partially or completely filling said void spaces The porosity of a material is defined as the ratio between the void volume and the total volume of the material, measured when the material is not filled with liquid. Non-limiting examples for porous materials are foams such as polyurethane, HIPE (see for example PCT patent application WO94/13704), superabsorbent foams and the like, fiber assemblies such as meltblown, spunbond, carded, cellulose webs, fiber beds and the like, porous particles such as clay, zeolites, and the like, geometrically structured materials such as tubes, balloons, channel structures etc. Porous materials might absorb liquids even if they are not hydrophilic. The porosity of the materials is therefore not linked to their affinity for the liquid that might be absorbed.

The term "substantially geometrically saturated" as used herein refers to a member in which at least 90% of the macroscopic void volume of the member are geometrically saturated, preferably at least 95% of the macroscopic void volume of the device are geometrically saturated, more preferably 97% of the macroscopic void volume of the device are geometrically saturated, most preferably 99% of the macroscopic void volume of the device are geometrically saturated.

In one embodiment of the present invention, the device for handling urine is a disposable absorbent article such as a diaper, a training pant, an adult incontinence device, or the like. Such an absorbent article may further comprise a liquid pervious topsheet, a liquid impervious backsheet at least partially peripherally joined to the topsheet. The absorbent article may further comprise an absorbent core which may serve as a storage member for the body liquid. Topsheets, backsheet, and absorbent cores suitable for the present invention are well known in the art. In addition, there are numerous additional features known in the art which can be used in combination with the absorbent article of the present invention such as for example closure mechanisms to attach the absorbent article around the lower torso of the wearer.

METHODS

Unless stated otherwise, all tests are carried out at about 32° C.+/−2° C. and at 35+/−15% relative humidity.

Unless stated otherwise, the synthetic urine used in the test methods is commonly known as Jayco SynUrine and is available from Jayco Pharmaceuticals Company of Camp Hill, Pa. The formula for the synthetic urine is: 2.0 g/: of KCl; 2.0 g/l of Na2SO4; 0.85 g/l of (NH4)H2PO4; 0.15 g/l (NH4)H2PO4; 0.19 g/l of CaCl2; ad 0.23 g/l of MgCl2. All of the chemicals are of reagent grade. The pH of the synthetic Urine is in the range of 6.0 to 6.4.

Demand Absorbency Test

The demand absorbency test is intended to measure the liquid capacity of liquid handling member and to measure the absorption speed of liquid handling member against zero hydrostatic pressure. The test may also be carried out for devices for managing body liquids containing a liquid handling member.

The apparatus used to conduct this test consists of a square basket of a sufficient size to hold the liquid handling member suspended on a frame. At least the lower plane of the square basket consists of an open mesh that allows liquid penetration into the basket without substantial flow resistance for the liquid uptake. For example, an open wire mesh made of stainless steel having an open area of at least 70 percent and having a wire diameter of 1 mm, and an open mesh size of at about 6 mm is suitable for the setup of the present test. In addition, the open mesh should exhibit sufficient stability such that it substantially does not deform under load of the test specimen when the test specimen is filled up to its full capacity.

Below the basket, a liquid reservoir is provided. The height of the basket can be adjusted so that a test specimen which is placed inside the basket may be brought into contact with the surface of the liquid in the liquid reservoir. The liquid reservoir is placed on the electronic balance connected to a computer to read out the weight of the liquid about every 0.01 sec during the measurement. The dimensions of the apparatus are chosen such that the liquid handling member to be tested fits into the basket and such that the intended liquid acquisition zone of the liquid handing member is in contact with the lower plane of the basket. The dimensions of the liquid reservoir are chosen such that the level of the liquid surface in the reservoir does not substantially change during the measurement. A typical reservoir useful for testing liquid handling members has a size of at least 320 mm×370 mm and can hold at least about 4500 g of liquid.

Before the test, the liquid reservoir is filled with synthetic urine. The amount of synthetic urine and the size of the liquid reservoir should be sufficient such that the liquid level in the reservoir does not change when the liquid capacity of the liquid handing member to be tested is removed from the reservoir.

The temperature of the liquid and the environment for the test should reflect in-use conditions of the member. Typical temperature for use in baby diapers are 32 degrees Celsius for the environment and 37 degrees Celsius for the synthetic urine. The test may be done at room temperature if the member tested has no significant dependence of its absorbent properties on temperature.

The test is setup by lowering the empty basket until the mesh is just completely immersed in the synthetic urine in the reservoir. The basket is then raised again by about 0.5 to 1 mm in order to establish an almost zero hydrostatic suction, care should be taken that the liquid stays in contact with the mesh. If necessary, the mesh needs to be brought back into contact with the liquid and zero level be readjusted.

The test is started by:
1. starting the measurement of the electronic balance;
2. placing the liquid handling member on the mesh such that the acquisition zone of the member is in contact with the liquid;
3. immediately adding a low weigh on top of the member in order to provide a pressure of 165 Pa for better contact of the member to the mesh.

During the test, the liquid uptake by the liquid handing member is recorded by measuring the weight decrease of the liquid in the liquid reservoir. The test is stopped after 30 minutes.

At the end of the test, the total liquid uptake of the liquid handing member is recorded. In addition, the time after which the liquid handling member had absorbed 80 percent of its total liquid uptake is recorded. The zero time is defined as the time where the absorption of the member starts. The initial absorption speed of the liquid handling member is from the initial linear slope of the weight vs. time measurement curve.

Member Liquid Distribution Test

This test is intended to measure the liquid distribution within a liquid handling member to be used in a device for handling urine. It is particulary suited for those members which are intended to acquire and temporarily store liquid. A result of this test Is the percentage of the x, y-dimension of the member over which the liquid has been distributed. This test methods may be equivalently applied to devices for handling urine which comprise such liquid handling member.

For the purpose of this test method, it is necessary to determine the liquid distribution over the x, y-dimension of the test specimen in terms of liquid weight per unit area at different times during the test procedure. A suitable test methods to determine the liquid distribution is x-ray imaging which is well known in the art. For example, such a method is described in an article entitled "Fluid distribution: Comparison of x-ray imaging data" by David F. Ring, Oscar Lijap, and Joseph Pascente in Nonwoven World magazine, summer 1995, at pp. 65–70. Generally, this procedure compares x-ray images of a wet and dry sample in order to calculate the liquid content. Suitable x-ray systems are available for example from LIXI Inc. of Downers Grove, Ill., USA, under the designation SA-100-2 SERIES, MODEL HLA-40-440M02. The system uses Bio-scan software from Optimas. The x-ray system may for example be operated with an exposure time of two second, with a tube voltage of 50 kV, and a current of 12 mA. It is to be noted, however, that for exposure time, tube voltage, and current different values have to be chosen depending on the specific properties of the test specimen to be examined.

The following description is adopted for devices for handling body liquids of the baby diaper type, and in particular for device is intended for babies in the weight range of about 9–18 kg. Nonetheless, the skilled person will be able to readily adopt it for other purposes, such as for other sizes, or adult incontinence applications.

The test specimen is arranged to lie flat on a liquid permeable large mesh support structure. Generally, it is preferred for this test that the test specimen, i.e. the liquid handling member which is to be tested, is separated from the device of which it is a member. Only if separation from the device would interfere substantially with the liquid handling of the test specimen, the device in its entirety is arranged lie flat on the mesh structure. Any other member which is intended to give the device a three-dimensional shape such as for example elastification is to be de-activated before this test for example by being removed from the device. The test specimen is fixed to the support surface with fixation means which do not negatively impact the fluid handling such as for example adhesive tapes. Also, the mesh and fixation means have to be made from a material that does not substantially interfere with the x-ray measurement. For example, a suitable support surface may be made to from a rigid polymeric mesh having an open area of at least 30 percent. The wire mesh should be sufficiently rigid such that the wire mesh substantially does not deform under the weight of a fully loaded test specimen. Then, the support structure is positioned such that the longitudinal dimension of the test specimen forms an angle of 15 degrees with the horizontal.

For analysis of the liquid distribution within the test specimen, the x, y-dimension of the test specimen is divided up into N compartments each of which should have substantially the same surface area and substantially the same dimensions in the x- and the y-direction. The total number of compartments, N, should be at least 50. From the x-ray analysis, the liquid distribution in grams of liquid per surface area is obtained for each of the compartments. The liquid content of each of the compartments is been determined by multiplying the liquid distribution in grams of liquid per surface area by the actual surface area of the respective compartment.

As the first step of this test method, the liquid distribution over the entire test specimen prior to loading is determined using the above x-ray method.

During the second step of this test, the test specimen is loaded with a single gush of synthetic urine at its intended loading point. For devices of the above-mentioned size, the gush size is defined to be 75 ml. This volume reflects the average gush size for toddlers of the above specified weight range. If the test specimen is a member of a device which is intended for different application such as for example adult incontinence devices, it will be readily apparent to the skilled person to accordingly adopt the gush volume. Irrespective of the gush size, the gush volume should not be delivered to onto the test specimen at a rate which is higher than the actual liquid acquisition rate of the test specimen. Any test liquid which is not acquired by the test specimen during this test, such as for example by running of from the surface of the test specimen or by dripping through the test specimen and subsequently through the support structure, is connected in the liquid receptacle positioned below the support structure and is immediately moved away from the test specimen such that this liquid does not contribute to the liquid content in the final x-ray analysis.

The test liquid is dispensed from a 6 mm inner diameter flexible tube, such as NORPREN A60G (6404-17), available from Cole Palmer Instrument Co., IL, US connected to test a liquid metering pump, such as digital pump, No. G-07523-20, having an easy load pump head, No. G-07518-02, both by Cole Parmer Instrument Co., IL, US, with the pump control unit to allow start and stop of the pump based upon electrical signals. The test liquid is dispensed into a cylinder which is joined the opening of the Plexiglas plate.

As the third step of this test, the liquid content of all of the N compartments of the test specimen is determined again thirty seconds after the start of dispensing the synthetic urine onto the test specimen.

The liquid uptake in each compartment is obtained by subtracting the initial liquid content of each compartment from its final liquid content For the purpose of this test, a compartment belongs to the area of liquid distribution if the liquid uptake of the compartment is more than a tenth of the gush volume divided by N. The total number of compartments belonging to the area of distribution is referred to as M.

As a result of this test, the percentage of the x, y-dimension of the test specimen over which the test liquid has been distributed is obtained by dividing the number of compartments belonging to the area of liquid distribution, M, by the total number of departments, N, and multiplying by 100. The percentage of the x-, y-dimension of the test specimen over which the test liquid has been distributed is also referred to as the distribution ratio.

As a further result of this test, the liquid distribution length in x-dimension is obtained as the longest extension of the area over which liquid has been distributed according to the above dimension.

What is claimed is:

1. A liquid handling member and device for handling urine, said liquid handling member having an x, y-dimension at least 60 square centimeters, said liquid handling member comprising a porous bulk region wrapped by a wall region, said bulk region comprising a material selected from the group consisting of fibers, particulates, foams, spirals, films, corrugated sheets, or tubes, wherein said liquid handling member has a first gush distribution ratio of at least 80 percent of said x, y-dimension.

2. A liquid handling member according to claim 1, wherein said liquid handling member has a z-direction dimension of less than 30 mm.

3. A liquid handling member according to claim 1, wherein said liquid handling member has a y-direction dimension of less than 100 mm.

4. A liquid handling member according to claim 1, wherein said liquid handling member has a demand absorbency liquid capacity of at least 50.

5. A liquid handling member according to claim 1, wherein said liquid handling member has a trans-planar permeability of at least 10 Darcy.

6. A liquid handling member and device for handling urine according to claim 1 wherein said handling member is an acquisition member for temporary storage of the acquired urine.

7. A liquid handling member and device for handling urine, said liquid handling member having an x-dimension at least 15 centimeters, said liquid handling member comprising a porous bulk region wrapped by a wall region, said bulk region comprising a material selected from the group consisting of fibers, particulates, foams, spirals, films, corrugated sheets, or tubes, wherein said liquid handling member has a first gush distribution length of at least 80 percent of said x-dimension.

8. A liquid handling member and device for handling urine according to claim 7 wherein said liquid handling member and device is an acquisition member for temporary storage of the acquired urine.

9. A device for handling urine according to claim 8, wherein said device further comprises a second member for ultimate storage of the acquired urine.

10. A device for handling urine according to claim 8, said device having a z-dimension substantially perpendicular to the surface of the acquisition region in the vicinity of the loading point of said device wherein said z-dimension of said device is less than 30 millimeters.

11. A device for handling urine according to claim 8, said device having a y-dimension substantially tangential to the surface of said acquisition region in the vicinity of the intended loading point of said device and perpendicular to the longitudinal dimension of said device wherein said y-dimension is less than 100 millimeters.

12. A device for handling urine according to claim 8, wherein said device is a disposable absorbent article.

13. A device for handling urine according to claim 12, wherein said device is a disposable diaper.

* * * * *

UNITED STATES PATENT AND TRADEMARK OFFICE
CERTIFICATE OF CORRECTION

PATENT NO. : 6,764,476 B1
DATED : July 20, 2004
INVENTOR(S) : Ehrnsperger et al.

It is certified that error appears in the above-identified patent and that said Letters Patent is hereby corrected as shown below:

Column 1,
Line 20, delete "bed-ridden" and insert -- bedridden --.

Column 3,
Line 53, before "most", delete "is".
Line 58, delete "180" and insert -- 160 --.

Column 4,
Line 11, after "hereinafter", delete "," (the comma) and insert -- . -- (a period).

Column 5,
Line 20, delete "Ehrnnsperger" and insert -- Ehrnsperger --.
Line 23, delete "Ehrnspergeret" and insert -- Ehrnsperger et --.

Column 6,
Line 25, after "changing", delete "is" and insert -- its --.
Line 34, after "spaces", insert -- . -- (a period).

Column 7,
Line 13, after "CaCl2;", delete "ad" and insert -- and --.

Column 8,
Line 30, delete "particulary" and insert -- particularly --.

UNITED STATES PATENT AND TRADEMARK OFFICE
CERTIFICATE OF CORRECTION

PATENT NO. : 6,764,476 B1
DATED : July 20, 2004
INVENTOR(S) : Ehrnsperger et al.

It is certified that error appears in the above-identified patent and that said Letters Patent is hereby corrected as shown below:

Column 10,
Line 3, after "content", insert -- . -- (a period).
Line 39, after "50", insert -- milliliters --.

Signed and Sealed this

Fourth Day of April, 2006

JON W. DUDAS
*Director of the United States Patent and Trademark Office*